United States Patent
Hull, Jr. et al.

(10) Patent No.: US 6,874,394 B1
(45) Date of Patent: Apr. 5, 2005

(54) CONTINUOUS METHOD OF PROVIDING INDIVIDUAL SHEETS FROM A CONTINUOUS WEB

(75) Inventors: Raymond J. Hull, Jr., Hampton, NJ (US); Lai-Hing Louie, Kendall Park, NJ (US); Sharon Ryan, Pennington, NJ (US); Hans Werner Schoelling, Ennepetal (DE)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/343,759

(22) Filed: Jun. 30, 1999

(51) Int. Cl.$^7$ .............................................. B26D 3/00
(52) U.S. Cl. ................................ 83/13; 83/660; 225/2
(58) Field of Search ...................... 83/13, 660; 604/15, 604/378, 904, 383, 385.1; 156/191, 192; 225/2

(56) References Cited

U.S. PATENT DOCUMENTS

| | | | |
|---|---|---|---|
| 3,205,750 A | 9/1965 | Strange | 83/660 |
| 3,716,132 A | 2/1973 | Lewyckyj | 206/58 |
| 3,796,219 A * | 3/1974 | Hanke | 604/48 |
| 4,342,314 A * | 8/1982 | Radel et al. | 604/370 |
| 4,437,373 A | 3/1984 | Van Der Meulen | 83/346 |
| 4,816,100 A | 3/1989 | Friese | 156/191 |
| 4,929,226 A | 5/1990 | Focke et al. | 493/343 |
| 5,185,010 A * | 2/1993 | Brown, Jr. | 604/374 |
| 5,571,361 A | 11/1996 | Stuerzel | 156/252 |
| 5,688,257 A * | 11/1997 | Olsen | 604/904 |
| 5,728,446 A * | 3/1998 | Johnston et al. | 604/378 |
| 5,755,906 A * | 5/1998 | Achter et al. | 604/385.1 |
| 5,761,982 A | 6/1998 | Abt et al. | 83/861 |
| 5,817,271 A | 10/1998 | Congleton et al. | 264/400 |
| 5,873,971 A * | 2/1999 | Balzar | 604/904 |
| 5,928,184 A * | 7/1999 | Etheredge et al. | 604/904 |
| 6,228,462 B1 * | 5/2001 | Lee et al. | 604/904 |

FOREIGN PATENT DOCUMENTS

| | | |
|---|---|---|
| DE | 44 09 405 A1 | 9/1994 |
| DE | 43 39 480 A1 | 5/1995 |
| DE | 196 41 144 A1 | 4/1998 |
| EP | 0 514 951 A1 | 11/1992 |
| GB | 2 276 354 A | 9/1994 |
| NL | 7211898 | 8/1972 |
| WO | WO 96/19313 | 6/1996 |
| WO | WO 97/23398 | 7/1997 |

OTHER PUBLICATIONS

PCT International Search Report PCT/US00/12981.

* cited by examiner

Primary Examiner—M. Rachuba

(57) ABSTRACT

A method for separating a supply of material into distinct sections of material, while controlling the position and orientation of these distinct sections during further manipulation in a continuous process is disclosed. The method includes forming a line of weakness comprising perforations and scores extending substantially from the first edge to the second edge and applying a force substantially parallel to the length of the web sufficient to separate an individual sheet from the web at the line of weakness.

3 Claims, 4 Drawing Sheets

CONTINUOUS METHOD OF PROVIDING INDIVIDUAL SHEETS FROM A CONTINUOUS WEB

CROSS-REFERENCE TO RELATED APPLICATIONS

This invention is related to the following co-pending applications: U.S. Ser. No. 09/345,090, entitled "Multilayered Apertured Film Wrapping Element for Absorbent Articles"; U.S. Ser. No. 09/345,089, entitled "Heterogeneous Apertured Film Wrapping Element for Absorbent Articles"; U.S. Ser. No. 09/343,760, entitled "Domed Tampon with Surfactant-Treated Cover"; U.S. Ser. No. 60/141,688, entitled "Sealing Roller and Sealing Roller Element, Particularly for Producing a Tampon for Feminine Hygiene and Method Therefore"; and U.S. Ser. No. 60/141,690, entitled "Tampon for Feminine Hygiene and Process and Apparatus for its Production", all filed Jun. 30, 1999.

FIELD OF THE INVENTION

The present invention relates to a continuous method of providing individual sheets from a web having a substantially infinite web. The method involves forming a line of weakness comprising perforations and scores. The method is particularly useful in continuous processes used to make individual articles by separating a substantially infinite length of web into individual sheets of material.

BACKGROUND OF THE INVENTION

With current technology, continuous manufacturing processes can produce up to 900 products per minute and more. The high speeds can magnify problems of handling materials due to the materials' interaction with machine contamination, machine wear, and other typical production altering variables. In addition to the complexities existing from high speeds, most manufacturing processes consists of assembling a plurality of different elements to make a final product. As processing speeds and the number of elements required in an assembly increase, the ability to produce quality articles within their specifications becomes increasingly difficult. To manage this difficulty, sophisticated control and registration systems have been developed. U.S. Pat. Nos. 4,264,957 and 4,361,260 disclose two such systems. Many of the known systems employ the use of electrical equipment, such as computers and sensors, which require on-going maintenance and energy costs.

Friese, U.S. Pat. No. 4,816,100 and related patents, discloses a simple, yet effective, method of controlling the position of discrete sections of nonwoven materials as the sections are separated from a stock roll and further manipulated. The method consists of the following steps: perforating the material transversely to its longitudinal direction, thereby maintaining strands of material between the perforated regions; optionally stretching the strands of material; and then breaking the strands by stressing the strands of material beyond their tensile strength. By only partially separating the section of material, control is maintained prior to total separation, thereby minimizing the opportunity for the material to become skewed, or otherwise out of position as it continues through the process. The time period and locations along a continuous process between the partial and total separation is fairly unlimited.

While the invention of Friese is useful with nonwoven materials, other materials, such as apertured films may not separate as effectively. Partially severed nonwoven webs are relatively controllable during further severing. The unsevered strands of material will not elongate significantly, and the partially separated section of material remains controlled during final separation. Unfortunately, it has been discovered that more continuous webs, including apertured films, are less controllable in the process of Friese.

Thus, a need exists for simple and effective methods for controlling the separation of wide variety of materials in a continuous process.

SUMMARY OF THE INVENTION

The object of the present invention is to provide a method for separating a supply of material into distinct sections of material, and controlling the position and orientation of the distinct sections during further manipulation in a continuous process.

In accordance with one embodiment of the resent invention, there has now been provided a method for providing individual sheets from a web having opposed, first and second edges and a substantially infinite length. The method includes forming a line of weakness comprising perforations and scores extending substantially from the first edge to the second edge and applying a force substantially parallel to the length of the web sufficient to separate an individual sheet from the web at the line of weakness.

In accordance with a second embodiment of the present invention, there has now been provided a method of providing individual sheets from a web having opposed, first and second edges and a substantially infinite length. The method includes (1) providing a knife and a knife abutting means, both having a web contacting surface, wherein at least one of the knife and abutting means web contacting surfaces contains a plurality of surface continuities and a plurality of surface discontinuities having a depth and a lateral width; (2) positioning a first portion of the web in a nip between the web contacting surfaces, wherein a second portion of the web extending beyond the contacting surfaces defines an individual sheet; (3) converging the knife and the knife abutting means, thereby perforating the web in regions corresponding to the surface continuities and scoring the material in regions corresponding to the surface discontinuities; and (4) applying a force substantially parallel to the length of the web sufficient to separate the individual sheet from the web at the line of weakness.

In accordance with a third embodiment of the present invention, there has now been provided a method of manufacturing a tampon. The method includes unwinding a web of liquid-permeable, thermoplastic apertured film, the web having opposed first and second edges and a substantially infinite length; forming a line of weakness comprising perforations and scores extending substantially from the first edge to the second edge; applying a force substantially parallel to the length of the web sufficient to separate an individual sheet from the web at the line of weakness; positioning the individual sheet over an absorbent sliver; attaching the individual sheet to the absorbent sliver; forming the absorbent sliver into a tampon blank; and compressing the tampon blank to form a substantially cylindrical, compressed tampon having a cover comprising the individual sheet.

DETAILED DESCRIPTION OF THE INVENTION

The present invention provides a method and apparatus for separating sections of material from a supply of material through multiple steps in a continuous manufacturing process, while maintaining control of the sections. The total separation of a section of material comprises the following steps: severing a supply material in a plurality of discrete regions along a transverse axis, scoring the material residing between the severed regions along the same transverse axis, and then applying a force sufficient to fracture the scored regions, thereby separating the section of material from its supply.

As used in this specification and in the appended claims, score is defined to be a "non-through" cut, that is, less than 100% of a material's thickness is cut. In comparison, cut, sever, and perforate all involve a cut through the entire thickness of a material.

The means for achieving the individual steps of severing, scoring, and applying force, are broadly reaching and known to those skilled in the art. A representative, non-limiting list of useful techniques for severing and scoring, includes laser and/or ultrasonic cutting and controlled depth scoring, reciprocating knives and anvils with controlled travel distances, rotary knives and anvils containing discontinuities on their material contacting surfaces, water jets, and the like.

The apparatus of the present invention, which is also used in the preferred method, comprises a knife and a knife abutting means, wherein at least one of them contain a plurality of discontinuities on their material contacting surfaces. The discontinuities have a width and a depth, the depth required to be less than the thickness of the material being separated into sections. When a material is passed between the converging knife and knife abutting means as described above, the material is both perforated and scored along a transverse axis.

The perforated and scored material can then be transferred to subsequent positions in the process, maintaining its registration, and thereafter be totally separated as a discrete section for final operations thereon.

The perforated and scored material can be attached to an absorbent structure as generally disclosed in Friese, U.S. Pat. No. 4,816,100, or as disclosed in U.S. Ser. No. 60/141,688, filed Jun. 30, 1999, entitled "Sealing Roller and Sealing Roller Element, Particularly for Producing a Tampon for Feminine Hygiene and Method Therefor".

Figure 1:
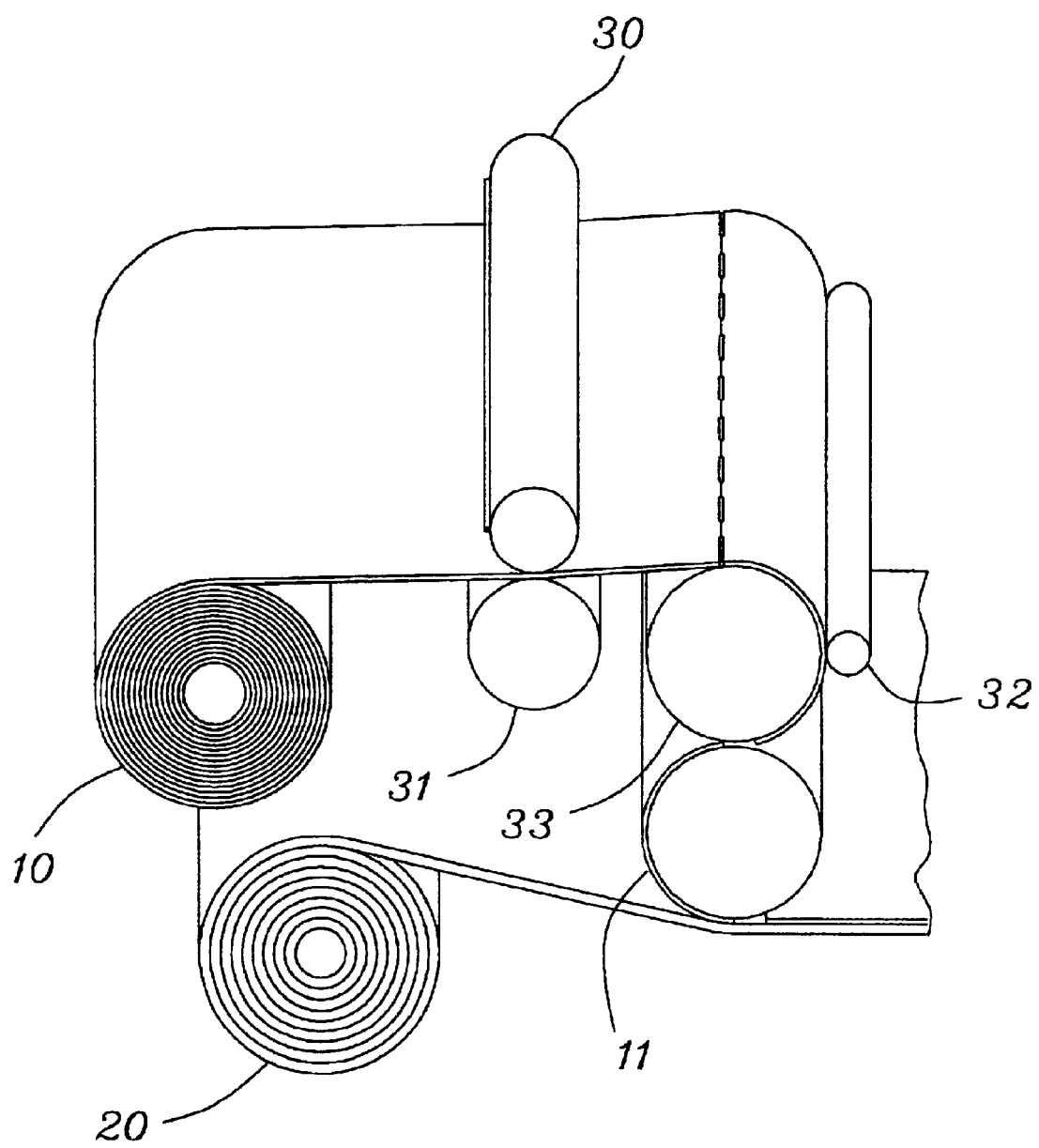
FIG. 1 represents a process of the present invention.

The following is a detailed description of the invention depicted in the Figures. FIG. 1 represents a process of manipulating multiple materials, with embodiments of the present invention shown in the separation of a section 11 of a first material 10 from a supply and joining the section 11 to a second material 20.

The total separation of the section 11 encompasses multiple steps. The first material 10 is severed in a plurality of discrete regions along a transverse axis and scored between the discrete regions. Then, a force is applied to the partially severed and scored material sufficient to completely separate a section 11.

The severing and scoring is preferably accomplished with a cylindrical knife 30 and cylindrical knife abutting means 31, wherein at least one of the knife or abutting means contacting surfaces contains a plurality of discontinuities. The discontinuities have a depth, which is less than that of the material being separated, thereby scoring the material in the corresponding regions.

Figure 4A:
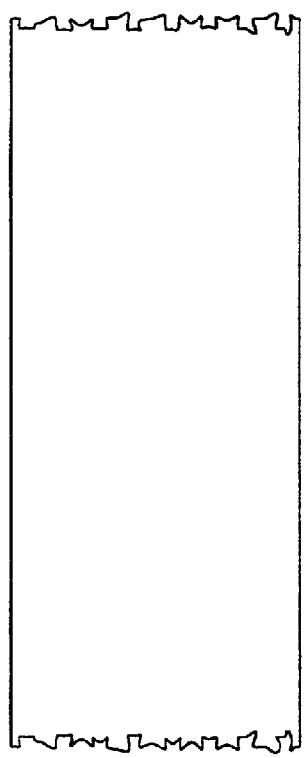
FIG. 4a represents an individual sheet of material separated from a web by using methods disclosed in the prior art.
Figure 4B:
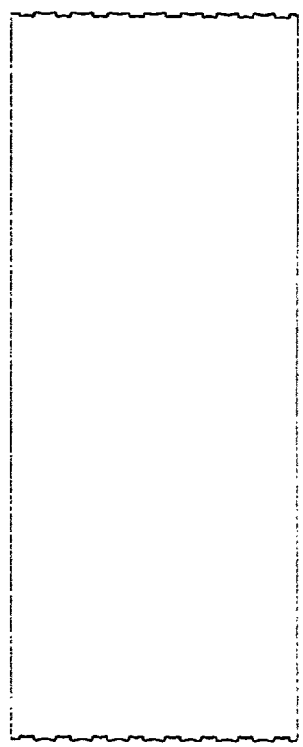
FIG. 4b represents an individual sheet of material separated from a web by according to an embodiment of the present invention.

The final step in separating the section of material after partially severing and scoring it, involves applying a force that will fracture the scored material. FIG. 1 shows the use of a contact roll 32 to apply this force. The contact roll 32 and the transfer roll 33 both have the same surface speed which is greater than that of the unseparated web. The web slides on and relative to the surface of transfer roll 33 until it is nipped between the transfer roll 33 and the contact roll 32. At that point the leading edge is accelerated to the surface speed of the transfer roll 33 and the contact roll 32 and the web separates at the perforated and/or scored line. Ideally the nip of the leading edge and resulting force to the web should be applied parralell to the web lenght. If the contact roll 32 has a full cylinderical surface any skewing of the leading edge of the web may be accentuated when the web is accelerated at the nip point. In a preferred embodiment the contact roll 32 will have an axial undercut in the surface timed to coincide with the leading edge of the web. The nip will then take place at a point past the leading edge of the web but before the perforated and or scored line. In this case any skewing of the leading edge or leading fibers or roughness as shown in FIGS. 4a and 4b will not be exaggerated. The method of applying force to the scored material may, but need not, be achieved by adjacent rolls having varying surface speeds.

Figure 2:
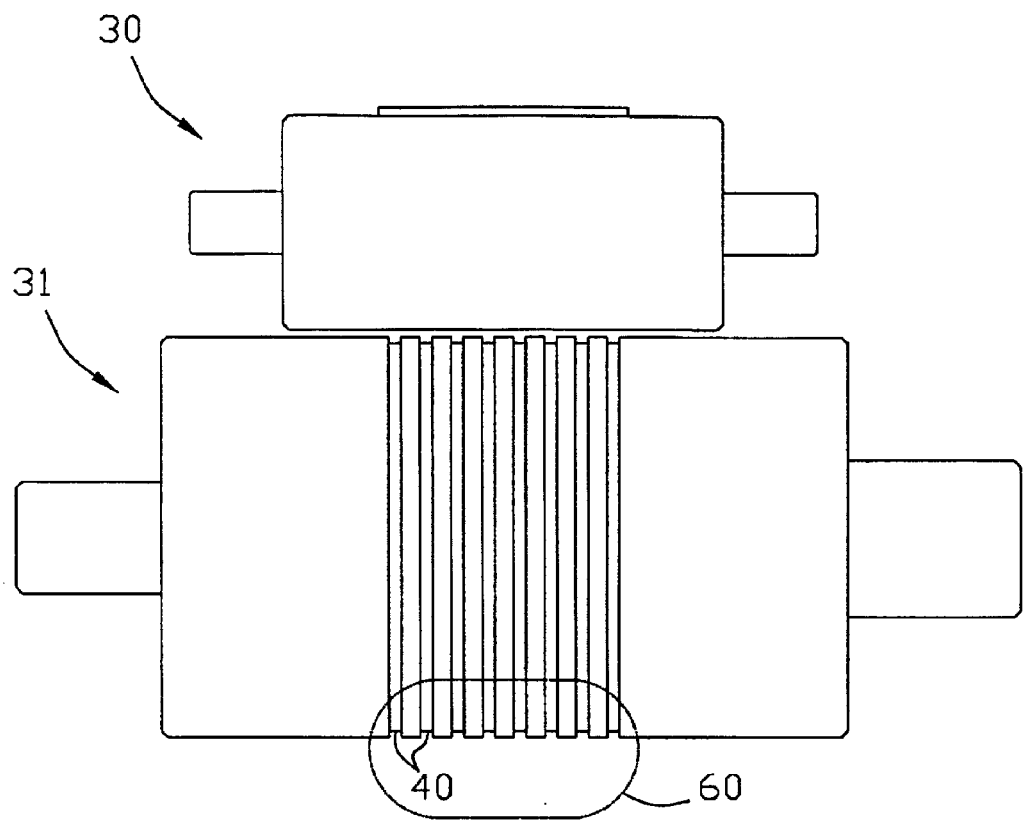
FIG. 2 depicts a front view of the knife and knife abutting means used in a process according to one embodiment of the present invention.
Figure 3:
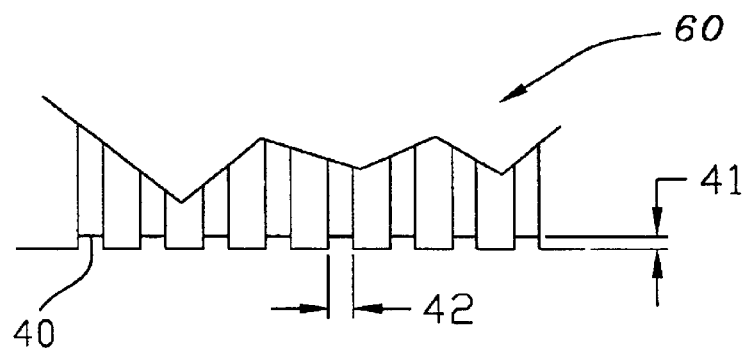
FIG. 3 represents an enlarged view of the web contacting surface of the knife abutting means of FIG. 2.

The details of the knife 30 and knife abutting means 31 can be seen in FIGS. 2 and 3. FIG. 2 shows the preferable arrangement of the present invention, where only one of the surfaces contains discontinuities 40, that being the knife abutting means 31. FIG. 3 shows the magnification zone 60 taken from FIG. 2. The discontinuities 40 are shown with a depth 41 and a width 42. As shown in FIG. 3, the discontinuities 40 are preferably spaced in a uniform fashion. However, the discontinuities can be spaced in a random fashion, or in an ordered random fashion, such as spaced at a first spacing proximate the ends and a second spacing proximate the center, or vice versa.

The depth 41 of the discontinuities is chosen to be less than about 95% of the material's thickness being separated. Preferably, the depth 41 is from about 10% to about 75% of the material's thickness. The width 42 of the discontinuities is from about 0.5 to about 6 mm; preferably from about 2 to about 4 mm. As with the spacing, the widths and depths of the discontinuities can be uniform, non-uniform, or a combination thereof.

FIGS. 2 and 3 depict the discontinuities 40 with a U-shaped cross section. The cross section of the discontinuities can be altered to yield greater or lesser depth variations along the length of a score. Other possible cross sections include discontinuities with a radius at the material contacting surface, and discontinuities that have a greater width at the material-contacting surface than the width distal to the material-contacting surface, such as a semi-hexagon.

The method and apparatus of the present invention will work effectively with a wide variety of materials, such as polymeric films, fibrous nonwovens, foams, paper, and woven fibers. The method is preferably used for separating sections of small gauge polymeric films from a supply roll. A representative, non-limiting list of polymeric films that may be separated with the present invention includes polyolefins, such as polypropylene and polyethylene; polyolefin copolymers, such as ethylene-vinyl acetate ("EVA"), ethylene-propylene, ethylene-acrylates, and ethylene-acrylic acid and salts thereof; halogenated polymers; polyesters and polyester copolymers; polyamides and polyamide copolymers; polyurethanes and polyurethane copolymers; polystyrenes and polystyrene copolymers; and the like. The polymeric films may be apertured and/or embossed. Films containing embossments and voids, such as apertures, and those otherwise exhibiting anistropic physical properties, may require engineering optimization of the discontinuity properties and spacing, in order to reduce any skewing that may take place with a partially separated section of material.

The present invention is especially useful for separating ductile materials and materials that exhibit a low elastic modulus and/or low toughness. Ductility as used in this specification, and in support of the appended claims, is the degree of permanent, non-recoverable deformation that has been sustained at fracture of a material. When separating materials in tension, ductility is the percent elongation of the material measured from a non-fractured state to a fractured state. Elastic modulus is a measure of a material's resistance to elastic deformation. Elastic deformation is recoverable or nonpermanent deformation, which will be eliminated when the stress, which caused the elastic deformation, is released from the material.

Figure 5:
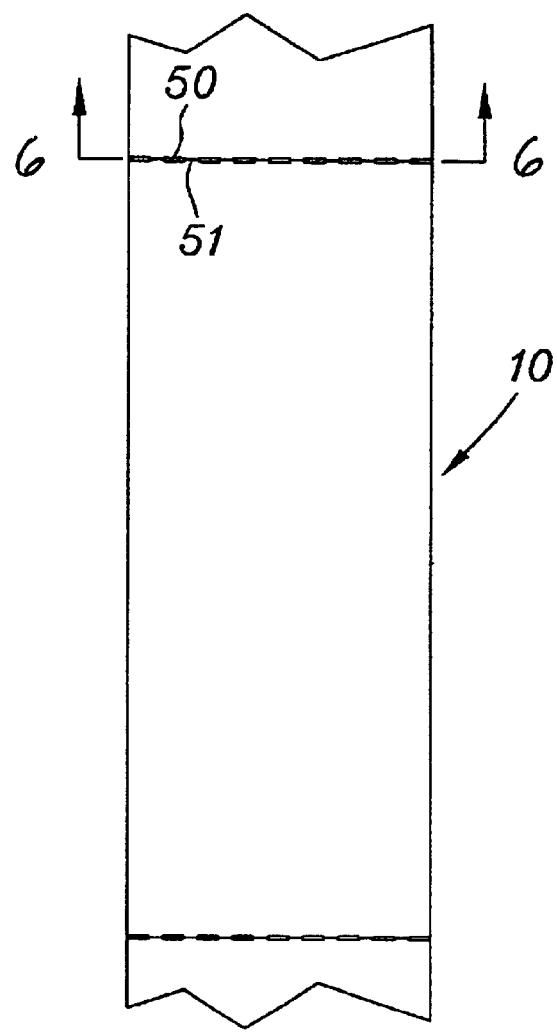
FIG. 5 represents a top view of the web.
Figure 6:
FIG. 6 represents a cross-section along line 6—6 of FIG. 5.

The invention is also well suited to separate laminated films, especially those with different physical characteristics in different laminate layers. In particular, this invention is especially suited to multilayered apertured films as described in Johnson et al., copending application U.S. Ser. No. 09/345,090, filed Jun. 30, 1999, entitled "Multilayered Apertured Film Wrapping Element for Absorbent Articles". As shown in FIGS. 5 and 6, the scores 51 between severed regions in a multilayered film may completely cut through one or more surface layers to reduce or eliminate their influence in the second severing step. This is especially effective when the intermediate layer of a three layered laminate is formed of a ductile material that has a low elastic modulus.

Otherwise, two disadvantages arise when processing ductile materials according to the Friese '100 method. One, is the scored material residing 51 between the perforations 50 will have a high percent elongation, thereby increasing the degrees of freedom the partially separated section has, resulting in decreased control. The second is the creation of ragged edges on the separated section, due to the significant non-recoverable elongation of the material between the perforations, prior to fracture.

FIG. 4a represents a section of material 11 separated from a supply of material by using methods disclosed by Friese in U.S. Pat. No. 4,816,100. Each edge of the section is fairly ragged due to elongation of the material in regions between the perforations. In comparison, FIG. 4b shows much cleaner section edges, due to the minimization of elongation resulting from the present invention.

The Friese method is also not ideally suitable for materials whose edges have a tendency, at the moment just after fracture, to "snap back" (recover), and disrupt the continuous process. The process disruption can consist of restarting the process, rejoining materials with transferring equipment, and cleaning the equipment from material build-up, which resulted from source material continually transferred to one location without being further transferred.

The method employed by the present invention minimizes the disadvantages described above, by minimizing the amount of material to fracture by way of scoring to a specified depth the material that is not perforated, while maintaining the control and registration of the partially separated section of material.

The method of the present invention is a simple, yet effective method of controlling the registration of raw materials in a continuous process. Due to this control, the method also provides an excellent alternative to sophisticated "cut and place" systems. By only partially separating a section of material, while minimizing the force required for final separation, registration is never lost. An additional embodiment to that already described includes adjoining the separated section of material, at a position downstream of the partial separation, to a second material. The method of adjoining a first material to a second material includes, but is not limited to, ultrasonics, hook and loop, adhesives, embossing, and pressure and heat.

The apparatus of the present invention contains elements to partially separate a section of material from a supply of material, and elements useful in completing the separation. The elements for the partial separation comprises a knife and knife abutting means, wherein at least one of their material contacting surfaces contains a plurality of discontinuities. The discontinuities have a depth, which is less than the thickness of the material being separated; therefore, imparts a score in the regions corresponding to the discontinuities. The knife and knife abutting means can be rotated, reciprocated, or both, when severing and scoring the material to be separated. If the knife and knife abutting means are cylindrical in form, then the discontinuities can cover the complete circumference and be directed towards and away from one another. Alternatively, the discontinuities can be placed at intermittent zones wherein the arc length dimension of the portion of the cylinder between discontinuities corresponds to the length of section intended to be separated, while the cylinders rotate with a fixed gap between their material contacting surfaces.

The knife and knife abutting means can be made of metal, polymers, wood, composites, ceramics, or combinations thereof. Preferably, the elements of the apparatus are constructed from hardened steel. The discontinuities on the material contacting surfaces can be made from any of the following, non-limiting techniques known to those skilled in the art, such as milling, lathing, engraving, and etching, such as by chemical or laser methods.

The disclosures of all US patents and patent applications, as well as any corresponding published foreign patent applications, mentioned throughout this patent application are hereby incorporated by reference herein.

The specification and embodiments above are presented to aid in the complete and non-limiting understanding of the invention disclosed herein. Since many variations and embodiments of the invention can be made without departing from its spirit and scope, the invention resides in the claims hereinafter appended

What is claimed is:

1. A method for the manufacture of a tampon comprising the steps of:
   a) providing a web of liquid-permeable, thermoplastic apertured film, the web having opposed first and second edges and a length;

b) forming a line of weakness comprising perforations and scores extending substantially from the first edge to the second edge;

c) applying a force substantially parallel to the length of the web sufficient to separate an individual sheet from the web at the line of weakness;

d) positioning the individual sheet over an absorbent sliver;

e) attaching the individual sheet to the absorbent sliver;

f) forming the absorbent sliver into a tampon blank; and g) compressing the tampon blank to form a substantially cylindrical, compressed tampon having a cover comprising the individual sheet.

2. The method of claim 1 wherein the attachment step comprises adhering the individual sheet to the absorbent sliver.

3. The method of claim 1 wherein the attachment step comprises heat sealing the individual sheet to the absorbent sliver.

\* \* \* \* \*